United States Patent [19]
Fearnot et al.

[11] Patent Number: 5,380,299
[45] Date of Patent: Jan. 10, 1995

[54] THROMBOLYTIC TREATED INTRAVASCULAR MEDICAL DEVICE

[75] Inventors: Neal E. Fearnot; Anthony O. Ragheb; William D. Voorhees, III, all of West Lafayette, Ind.

[73] Assignee: MED Institute, Inc., West Layfayette, Ind.

[21] Appl. No.: 114,261

[22] Filed: Aug. 30, 1993

[51] Int. Cl.$^6$ .............................................. A61M 5/32
[52] U.S. Cl. ........................................ 604/265; 623/1; 623/11
[58] Field of Search .................. 128/898; 604/890.1, 604/891.1, 892.1, 264, 265; 623/1, 11, 12

[56] References Cited

U.S. PATENT DOCUMENTS

| | | |
|---|---|---|
| 4,305,926 | 12/1981 | Everse et al. |
| 4,502,159 | 3/1985 | Woodroof et al. |
| 4,879,135 | 11/1989 | Greco et al. ............................. 623/1 |
| 4,909,799 | 3/1990 | Thulesius et al. ................... 604/265 |
| 4,917,686 | 4/1990 | Bayston ................................. 604/265 |
| 4,950,256 | 8/1990 | Luther ................................... 604/265 |
| 4,994,047 | 2/1991 | Walker et al. ........................ 604/265 |
| 5,004,461 | 4/1991 | Wilson .................................. 604/265 |
| 5,019,096 | 5/1991 | Fox, Jr. et al. ............................ 623/1 |
| 5,019,393 | 5/1991 | Ito et al. |
| 5,019,601 | 5/1991 | Allen .................................... 604/265 |
| 5,098,977 | 3/1992 | Frautschi et al. ...................... 604/96 |
| 5,135,516 | 8/1992 | Sahatjian et al. .................... 604/265 |
| 5,163,952 | 11/1992 | Froix. |
| 5,165,952 | 11/1992 | Solomon et al. ..................... 604/265 |
| 5,182,317 | 1/1993 | Winters et al. |
| 5,222,971 | 6/1993 | Willard et al. |
| 5,229,172 | 7/1993 | Cahalan et al. ....................... 427/536 |

OTHER PUBLICATIONS

The Merck Index, 10th edition, 1983 pp. 28,273–274.
Aoshima, R. et al. "Lifetimes of Immobilized UK on Silicone–Collagen Graft and Sulfonated Poly Vinylidene Fluoride", *Artificial Organs*, Aug. 1981, vol. 5, p. 307.
Aoshima, R. et al. "Sulfonated poly(vinylidene fluoride) as a biomaterial", *Journal of Biomedical Material Research*, 1982, vol. 16, pp. 289–299.
Kusserow, B. K. et al. "The Urokinase-Heparin Bonded Synthetic Surface", *Trans. Amer. Soc. Artif. Int. Organs*, 1971, vol. 17, pp. 1–5.
Kusserow, B. K. et al. "The Surface Bonded, Covalently Crosslinked Urokinase Synthetic Surface", *Trans. Amer. Soc. Artif. Int. Organs*, 1973, vol. 19, pp. 8–12.
Ohshiro, Takeshi et al. "Urokinase Immobilized on Medical Polymeric Materials", *Artificial Organs*, 1980, vol. 4, pp. 58–64.
Sugitachi, Akio, et al. "Antithrombogenicity of Immobilized Urokinase", *The International Journal of Artificial Organs*, 1978, vol. 1, No. 2, pp. 88–92.
Sugitachi, A. et al. "Antithrombogenicity of UK–Immobilized Polymer Surfaces", *Trans. Am. Soc. Artif. Intern. Organs*, 1980, vol. 26, pp. 274–278.

*Primary Examiner*—C. Fred Rosenbaum
*Assistant Examiner*—Chalin Smith
*Attorney, Agent, or Firm*—Richard J. Godlewski

[57] ABSTRACT

An intravascular medical device having a structure shaped and sized for introduction into the vascular system of a patient including a base material and a coating of a thrombolytic agent on the base material. The thrombolytic agent advantageously dissolves or breaks up the formation of thrombus on the surface of the structure when placed in the vascular system of a patient. The intravascular medical device also includes a antithrombogenic agent for inhibiting the formation of thrombus on the surface of the medical device. The method of treating a medical device with a thrombolytic agent includes providing a base material for the medical device along with a thrombolytic agent. The base material is dipped into the thrombolytic agent and then removed to allow the thrombolytic agent to dry on the surface thereof. The dipping and drying steps are repeated to increase the concentration or quantity of the thrombolytic agent on the device.

18 Claims, 4 Drawing Sheets

THROMBOLYTIC TREATED INTRAVASCULAR MEDICAL DEVICE

TECHNICAL FIELD

This invention relates generally to medical devices and, in particular, to an intravascular medical device treated with a thrombolytic agent.

BACKGROUND OF THE INVENTION

When medical devices such as catheters, wire guides, cannulae, stents, and the like are introduced into the vascular system of a patient and manipulated through the vessels thereof, the blood vessel wall is commonly disturbed or injured. Clot formation or thrombosis often results at the injured site, and the blood vessel can experience obstruction or closure. Should the medical device remain within the vessel for an extended period of time, thrombus often forms on the device as well. As a result, the patient risks complications such as heart attack, pulmonary embolism, and stroke.

One medical device such as an intravascular stent provides a useful adjunct to percutaneous transluminal catheter angioplasty (PTCA), particularly in the case of acute or threatened vessel closure after an angioplasty procedure. A problem with the use of intravascular stents is that stent implantation requires aggressive and precise antiplatelet and anticoagulation therapy typically via systemic administration. Still, the incidence of thrombotic complications remains significant. Furthermore, a side effect of this systemic antiplatelet and anticoagulation therapy is increased blood loss at the percutaneous entry site where the stent is introduced into the vascular system. As a result, the incidence of bleeding complications remains significant.

SUMMARY OF THE INVENTION

The foregoing problems are solved and a technical advance is achieved in an illustrative intravascular medical device having a structure shaped and sized for introduction into the vascular system of a patient. The structure includes a base material such as stainless steel with a coating of a thrombolytic agent such as urokinase on the base material to advantageously dissolve or break up any formation of thrombus formed on the surface of the structure. Urokinase is a well-known systemic thrombolytic agent administered to patients. However, the application of urokinase as a coating on the surface of an intravascular medical device or the inclusion of the thrombolytic agent in the formation of the base material has not been previously examined. The application of the thrombolytic agent to the base material with an antithrombogenic agent, such as heparin, further minimizes the formation of thrombus on the medical device when positioned into the vascular system of a patient.

The base material comprises at least one from a group consisting of a metal, a polymer, and a biologically derived material such as collagen.

The thrombolytic agent advantageously includes one or more from a group consisting of urokinase, streptokinase, and a tissue plasminogen activator. The antithrombogenic agent comprises at least one or more from a group of heparin, hirudin, and an antiplatelet.

When the antithrombogenic and thrombolytic agents are applied to the surface of a base material, a primer coating such as cellulose ester or cellulose nitrate is applied to the surface of the medical device structure for adhering at least one of coating of the thrombolytic and antithrombogenic agents.

In an alternative embodiment of the present invention, the intravascular medical device can include a structure of which the base material and the thrombolytic agent are combined together. The antithrombogenic material is then applied or added to further enhance the ability of the device to minimize and/or dissolve the formation of thrombus thereon.

The method of treating a medical device with a thrombolytic agent comprises providing a base material for the medical device along with the thrombolytic agent. The base material is treated with the thrombolytic agent to advantageously dissolve the thrombus on the surface of the medical device. The base material is advantageously dipped into a solution of the thrombolytic agent and then removed to allow the thrombolytic agent to dry thereon. The steps of dipping and drying the base material and the thrombolytic agent is repeated to form a desired concentration or quantity of thrombolytic agent on the base material. The method further includes providing a polymer or a biologically derived material and mixing the thrombolytic agent with the polymer or biologically derived material and applying the mixture to the base material.

DETAILED DESCRIPTION

Figure 1:
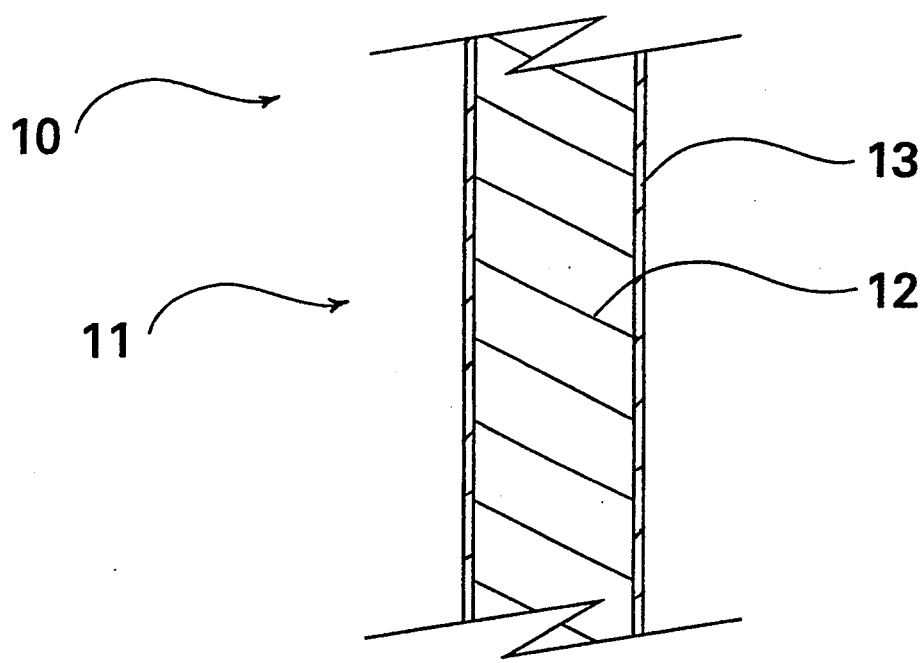
FIG. 1 depicts a longitudinally sectioned view of an intravascular medical device of the present invention with a thrombolytic coating on the structure of the device.

FIG. 1 depicts a longitudinally sectioned view of an intravascular medical device 10 such as a stent, catheter, wire guide, cannula, and the like having a structure 11 shaped and sized for introduction into the vascular system of a patient. The structure of a stent typically includes a formed wire such as the commercially available Gianturco-Roubin FLEX-STENT coronary stent from Cook Incorporated, Bloomington, Ind., for percutaneous introduction to a failed angioplasty site. The structure of a catheter, wire guide, cannula, and the like are also well-known and commercially available from Cook Incorporated as well as other medical device manufacturers. These intravascular medical devices are commonly inserted into the vasculature of a patient using well-known percutaneous surgical procedures. To advantageously remove the formation of thrombus on the medical device, the structure includes a thrombolytic agent 13 and a base material 12 treated with the thrombolytic agent. In FIG. 1, thrombolytic agent 13 is depicted as a coating on base material 12.

Base material 12 of the intravascular medical device includes any one of a number of different commercially available materials such as a metal, a carbon, a polymer, or a biologically derived material suitable for the formation of the structure. The metal comprises, amongst others, at least one from a group consisting of stainless steel, tantalum, nitinol, gold, platinum, inconel, and iridium, which are all commercially available metals or alloys used in the fabrication of medical devices. All of these metals are well-known to be biocompatible materials. The polymer comprises at least one from a group consisting of well-known cellulose acetate, cellulose nitrate, silicone, polyethylene teraphthalate, polyurethane, polyamide, polyester, polyorthoester, and a polyanhydride. Biologically derived material includes, by way of example, collagen.

Thrombolytic agent coating 13 comprises at least one from a group consisting of well-known and commercially available urokinase, streptokinase, and tissue plasminogen activators (tPA), which are applied to the base material of the device. These thrombolytic agents are well-known and typically administered systemically to dissolve, break up, or disperse thrombus.

Figure 2:
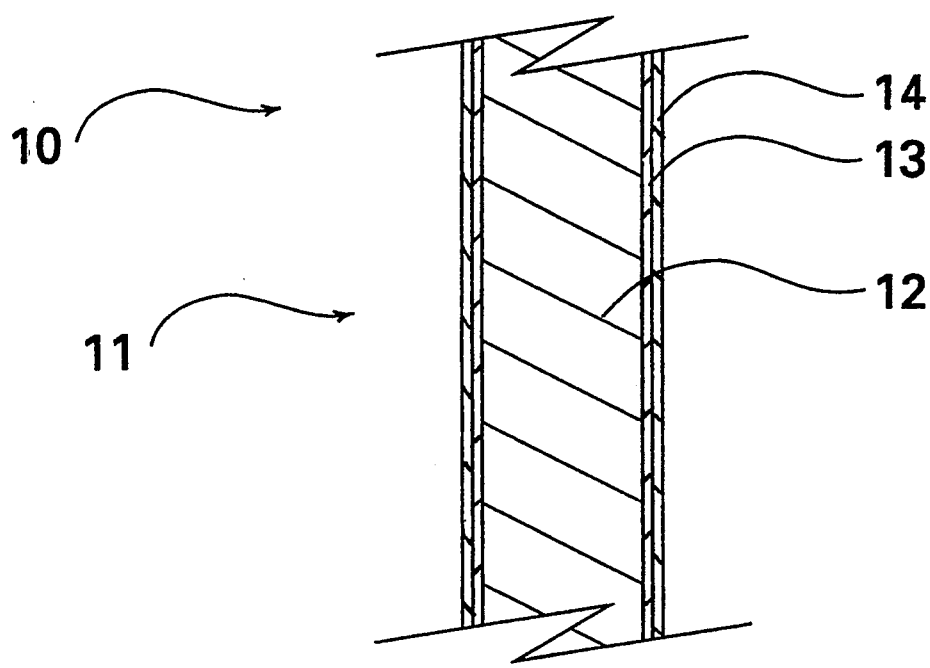
FIG. 2 depicts the medical device of FIG. 1 with a coating of an antithrombogenic agent on the base material of the device.

Depicted in FIG. 2 is medical device 10 of FIG. 1 with a second coating 14 of an antithrombogenic agent on base material 12. This antithrombogenic agent includes at least one from a group consisting of heparin, hirudin, and an antiplatelet for inhibiting the formation of thrombus on the medical device.

Figure 3:
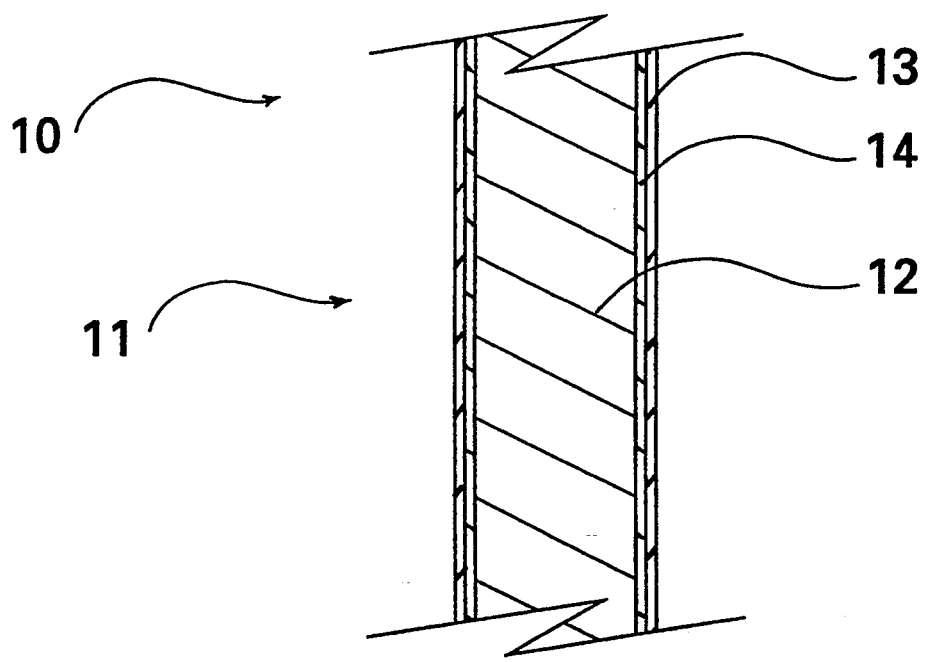
FIG. 3 depicts the medical device of FIG. 1 with a first antithrombogenic agent coating formed on the base material and a second thrombolytic agent coating formed thereon.

FIG. 3 depicts the medical device 10 of FIG. 1 with the antithrombogenic agent coating 14 formed first on base material 12 and then thrombolytic agent coating 13 formed on top of coating 14.

Figure 4:
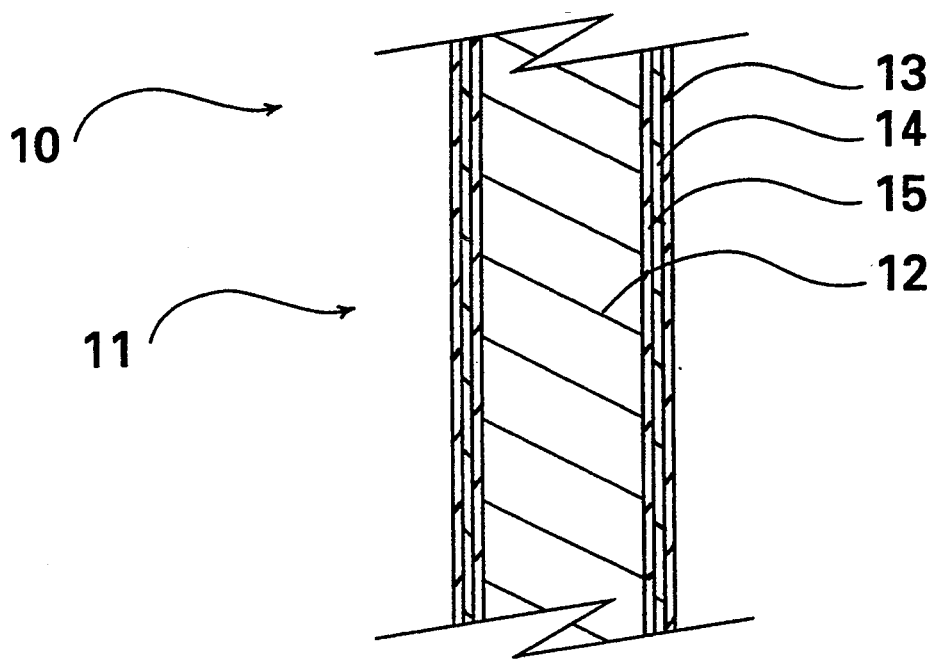
FIG. 4 depicts the medical device of FIG. 3 with a primer coating first applied to the base material for adhering the antithrombogenic and thrombolytic agent coatings to the base material.

FIG. 4 depicts medical device 10 of FIG. 3 wherein a primer coating 15 has been first applied to base material 12 for adhering the coatings of the antithrombogenic agent 14 and thrombolytic agent 13 to the base material. This primer material coating includes, for example, well-known and commercially available cellulose ester, cellulose nitrate, or a combination thereof.

Figure 5:
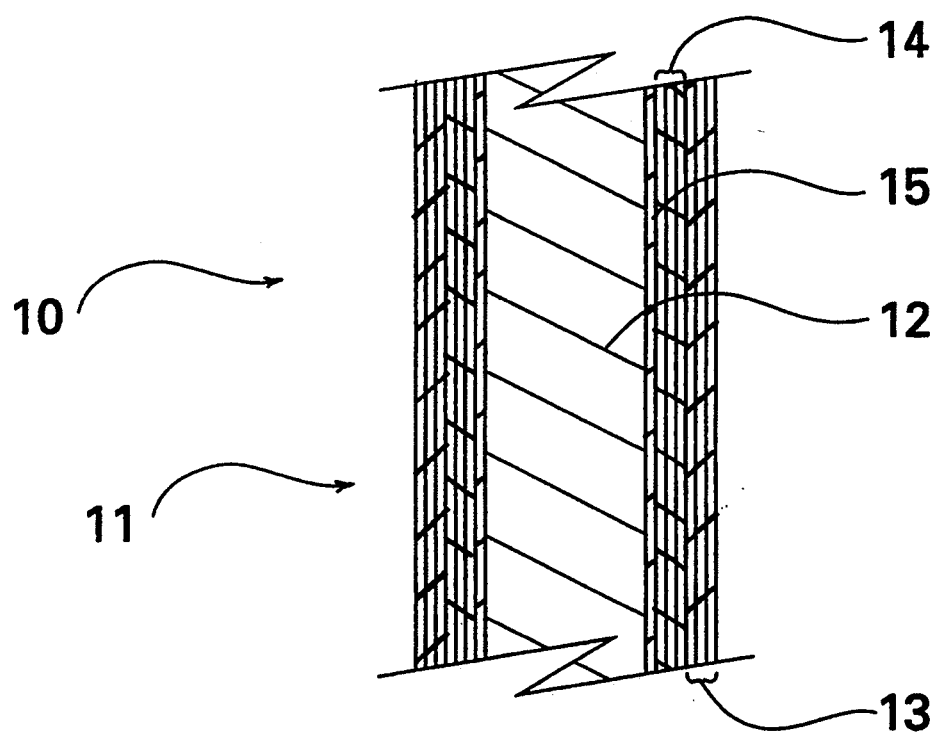
FIG. 5 depicts the medical device 10 of FIG. 3 with a primer coating and three separate layers each of the antithrombogenic and thrombolytic agent coatings applied thereto.

FIG. 5 depicts medical device 10 of FIG. 3 with primer coating 15 with three separate layers of antithrombogenic agent 14 and three separate layers of thrombolytic agent 13 applied thereover.

Although medical device 10 has been illustrated as having separate coatings of a thrombolytic agent 13 and antithrombogenic agent 14 applied thereto, it is to be understood and contemplated that medical device 10 can be formed by mixing the antithrombogenic agent, thrombolytic agent, and the base material together to form the basic structure of the device. A primer can also be applied to this mixture for facilitating the bonding of the two agents to the base material. Alternatively, the intravascular medical device of the present invention can also be a structure including any one or more of the aforementioned thrombolytic agents and a base material treated with the thrombolytic agent. It is also contemplated that the base material can also include carbon such as is associated with pacemaker leads. The base material and thrombolytic agent can be formed together and then extruded or molded to form the intravascular medical device as desired. The antithrombogenic agent can be applied in the form of a coating or, alternatively, included in the mixture as previously discussed.

The method of treating a device with a thrombolytic agent comprises the steps of providing a base material for the medical device along with providing a thrombolytic agent and treating the base material with the thrombolytic agent as will be described in more detail hereinafter. The step of treating the base material includes dipping the base material such as stainless steel into a solution of the thrombolytic agent such as urokinase. The base material is removed from the solution and the thrombolytic agent coating allowed to dry. The steps of dipping and drying the thrombolytic agent on the base material is then repeated as many times as necessary to establish a desired or quantity concentration of the thrombolytic agent. The method of treating a medical device with a thrombolytic agent also includes providing at least one of a group consisting of a polymer or a biologically derived material as previously described. The thrombolytic agent and the polymer or biologically derived material are mixed and then applied to the base material.

Figure 6:
FIG. 6 depicts the base material of a medical device which has been placed in human blood.

Depicted in FIG. 6 is base material 17 such as stainless steel of a medical device which has been placed in human blood. Red blood cells 18, crenated red blood cells 19, platelet aggregates 20, single platelets 21, and a large number of fibrin threads 22 have formed on the untreated base material when placed in, for example, human blood.

Figure 7:
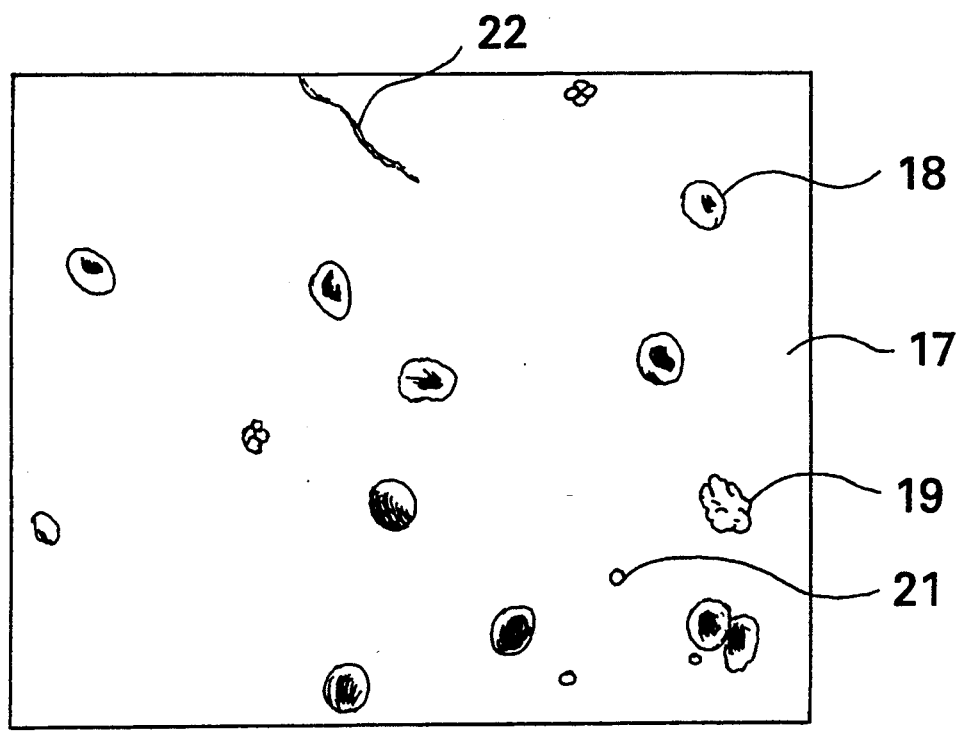
FIG. 7 depicts the base material of a medical device treated with antithrombogenic and thrombolytic agents which have been placed in human blood.

FIG. 7 depicts base material 17 treated with a thrombolytic agent as described herein. A much smaller number of red blood cells 18, crenated red blood cells 19, and platelets 21 adhered to and fibrin threads 22 formed on the treated base material. FIG. 7 illustrates samples of stainless steel treated with urokinase. The samples in FIGS. 6 and 7 have been magnified 1,500 times.

A description of the materials and method used with in-vitro thrombus deposition on three Gianturco-Roubin FLEX-STENT coronary stents from Cook Incorporated will now be described. In-vitro thrombus deposition on three Gianturco-Roubin coronary FLEX-STENT coronary stents was examined. The stents were 20–25 mm in length and designed to expand to 2.5–3.5 mm in diameter. One stent was made from 0.006" diameter stainless steel wire, a second from 0.006" diameter tantalum wire, and a third from coated 0.006" diameter stainless steel wire. The third stent was coated with a layer of primer (designated 35066C and commercially available from STS Biopolymers, Inc., Rush, N.Y.) followed by 3 layers of heparin in a cellulose polymer (Medicoat Heparin type 35066A, also commercially available from STS Biopolymers Inc.). After deployment, the third stent was further coated with urokinase (Abbokinase ™, urokinase for injection, 50,000 I.U./ml, commercially available from Abbot Laboratories, North Chicago, Ill.). The stent was dipped in the urokinase solution for approximately 5 minutes, dried in room air for approximately 30 minutes, dipped in urokinase solution for approximately 1 minute, dried in room air for approximately 30 minutes, dipped in urokinase solution for 5–10 seconds and dried in room air for 30 minutes before further handling. All three stents were radially expanded before being used in the thrombus deposition experiment, which will now be described.

Each stent was suspended from the cap of a 6 ml test tube for incubation in blood. Eighteen ml of human venous blood was collected in a series of three 6 ml vacutainer tubes, each containing 0.06 ml of heparinized normal saline (100 units of heparin/ml). The blood, containing 1 unit of heparin per ml, was then carefully poured into the incubation tubes and the caps suspending the stents were placed on these tubes. The tubes were positioned on an inclined turntable rotating at approximately 20 rpm in a 37 degree C. oven. The tubes were positioned so that the stent remained totally immersed in blood for the entire incubation period which lasted one hour. The tubes were positioned so as to rotate in a well-known manner. After the one hour incubation in blood, each stent was gently rinsed (2 dips of approximately 1-3 seconds duration each) in 37 degrees C. phosphate buffered saline and then fixed in 3 percent glutaraldehyde in phosphate buffered saline for at least 30 minutes before further processing. After standard preparation (post-fixation in osmium, dehydration, critical point drying and gold sputter coating) the stents were examined by scanning electron microscopy.

The surfaces of the uncoated stainless steel and tantalum stents were completely covered with a dense fibrin mesh containing platelets and red blood cells as depicted in FIG. 6. For each of these stents, there was some variability in this covering from region to region. However, there were no striking differences between the stainless steel and tantalum stents and the coverage was visually estimated to be near 100 percent.

The surface of the heparin-urokinase coated stent, as depicted in FIG. 7, appeared strikingly different. The vast majority (visually estimated at 90-95 percent) of the surface had only a few adherent red blood cells and a rare adherent platelet. There was also some variability in this covering and a visually estimated 5 to 10 percent of the surface had a slightly denser layer of adherent red blood cells 18 with a few platelets 21 and an occasional fibrin thread 22.

The most striking difference between the coated and uncoated stents was the fibrin deposition. Nearly 100 percent of the surface of the uncoated stents appeared covered with fibrin in contrast to a visually estimated fibrin coverage of only 1-2 percent for the coated stent.

Heparin is a mucopolysaccharide anticoagulant typically obtained from porcine intestinal mucosa or bovine lung. Heparin acts as a thrombin inhibitor by greatly enhancing the effects of the blood's endogenous antithrombin III. Thrombin, a potent enzyme in the coagulation cascade, is key in catalyzing the formation of fibrin. Therefore, by inhibiting thrombin, heparin inhibits the formation of fibrin thrombi. However, heparin's inhibition of thrombin and fibrin formation is not 100 percent as evidenced by the fibrin deposition on uncoated stents in heparinized blood. Furthermore, heparin does not have fibrinolytic activity.

Urokinase is a plasminogen activating enzyme typically obtained from human kidney cell cultures. Urokinase catalyzes the conversion of plasminogen into the fibrinolytic plasmin which breaks down fibrin thrombi.

It is highly probable that both the heparin and urokinase on the coated stent contributed to the dramatic reduction in fibrin deposition on this stent. It has not been determined which of these agents may have had the greater effect. Moreover, it has not been determined whether the effects were localized near the surface of the stent or whether the delivery of heparin or urokinase may have caused anticoagulant and/or fibrinolytic effects respectively on the entire 6 ml of blood in which the stent was incubated.

It is to be understood that the above-described thrombolytic treated intravascular medical device is merely an illustrative embodiment of the principles of this invention and that other thrombolytic treated intravascular medical devices may be devised by those skilled in the art without departing from the spirit and scope of this invention. In the method of treating the device, it is contemplated that treating the device includes spraying, impregnating, or mixing the thrombolytic agent on, in, or with the base material.

What is claimed is:

1. An intravascular medical device comprising:
 a structure shaped and sized for introduction into a vascular system of a patient, and structure including a base material and a homogeneous coating of a thrombolytic agent and at least one from a group consisting of a cellulose and a cellulose-based polymer on said base material.

2. The medical device of claim 1 wherein said base material comprises at least one from a group consisting of a metal, a carbon, a polymer, and a biologically derived material.

3. The medical device of claim 2 wherein said thrombolytic agent comprises at least one from a group consisting of urokinase, streptokinase, and a tissue plasminogen activator.

4. The medical device of claim 1 wherein said homogeneous coating further includes an antithrombogenic agent.

5. The medical device of claim 4 wherein said antithrombogenic agent comprises at least one from a group consisting of heparin, hirudin, and an antiplatelet.

6. The medical device of claim 5 wherein said cellulose-based polymer includes at least one from a group consisting of a cellulose acetate, a cellulose ester, and a cellulose nitrate.

7. The medical device of claim 2 wherein said metal includes at least one from a consisting of stainless steel, tantalum, nitinol, gold, platinum, inconel, and iridium.

8. An intravascular medical device comprising:
 a structure shaped and sized for introduction into a vascular system of a patient, said structure including a base material and a homogeneous coating of at least one from a group consisting of a thrombolytic agent and an antithrombogenic agent and at least one from a group consisting of a cellulose and a cellulose-based polymer on said base material.

9. The medical device of claim 8 further including a primer agent for adhering an other of said thrombolytic agent and said antithrombogenic agent to said base material.

10. The medical device of claim 9 wherein said thrombolytic agent comprises at least one from a group consisting of urokinase, streptokinase, and a tissue plasminogen activator.

11. The medical device of claim 9 wherein said antithrombogenic agent comprises at least one from a group consisting of heparin, hirudin, and an antiplatelet.

12. The medical device of claim 9 wherein at least one of said primer agent and said cellulose-based polymer comprises at least one from a group consisting of a cellulose acetate, a cellulose ester and a cellulose nitrate.

13. An intravascular medical device comprising:
 a structure shaped and sized for introduction into a vascular system of a patient, said structure including a thrombolytic agent and a base, homogeneous material including said thrombolytic agent and at least one from a group consisting of a cellulose, a cellulose acetate, a cellulose ester, and a cellulose nitrate.

14. The medical device of claim 13 wherein said structure includes an antithrombogenic agent.

15. The medical device of claim 14 wherein said structure includes a primer for adhering said antithrombogenic to said base material.

16. The medical device of claim 15 wherein said primer includes at least one of a group consisting of a cellulose, a cellulose acetate, a cellulose ester and a cellulose nitrate.

17. The medical device of claim 14 wherein said antithrombogenic agent comprises at least one from a group consisting of heparin, hirudin, and an antiplatelet.

18. The medical device of claim 13 wherein said thrombolytic agent comprises at least one from a group consisting of urokinase, streptokinase, and a tissue plasminogen activator.

* * * * *